United States Patent
Chodkowski et al.

(10) Patent No.: US 9,764,106 B2
(45) Date of Patent: Sep. 19, 2017

(54) UNIDIRECTIONAL FLEXION CLIP

(71) Applicant: KONINKLIJKE PHILIPS N.V., Eindhoven (NL)

(72) Inventors: Lauren Patricia Chodkowski, Pittsburgh, PA (US); Robert Willaim Baiko, Pittsburgh, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 422 days.

(21) Appl. No.: 14/379,092

(22) PCT Filed: Feb. 27, 2013

(86) PCT No.: PCT/IB2013/051554
§ 371 (c)(1),
(2) Date: Aug. 15, 2014

(87) PCT Pub. No.: WO2013/128377
PCT Pub. Date: Sep. 6, 2013

(65) Prior Publication Data
US 2016/0015923 A1    Jan. 21, 2016

Related U.S. Application Data

(60) Provisional application No. 61/604,168, filed on Feb. 28, 2012.

(51) Int. Cl.
*A61M 16/06* (2006.01)
*A62B 18/08* (2006.01)

(52) U.S. Cl.
CPC .... *A61M 16/0622* (2014.02); *A61M 16/0683* (2013.01); *A62B 18/084* (2013.01)

(58) Field of Classification Search
CPC .... A41D 13/1161; A44B 11/00; A61M 16/06; A61M 16/0683; A61M 16/142; A61M 2016/102; A61M 2205/0266; A61M 2205/3368; A61M 2205/35; A61M 2205/50; A61M 2205/502; A61M 2205/52; A61M 2205/581; A61M 2205/582;
(Continued)

(56) References Cited

U.S. PATENT DOCUMENTS

2008/0047560 A1    2/2008  Veliss
2009/0078268 A1*   3/2009  Stepan ............... A44B 11/00
                                                       128/207.11
(Continued)

FOREIGN PATENT DOCUMENTS

CN    1684733 A      10/2005
CN    101553270 A    10/2009
(Continued)

*Primary Examiner* — Annette Dixon
(74) *Attorney, Agent, or Firm* — Michael W. Haas

(57) ABSTRACT

A flexion coupling (50) for a respiratory interface (8) device is provided. The respiratory interface device includes a mask (10) and a support assembly (30) having at least one strap (40). The flexion coupling includes an elongated flexure body (52) with at least one mask coupling (54) and at least one strap coupling (56). The coupling may include a flexible softer first material (60) and an inflexible harder second material (62) in form of a plurality of elements (80) disposed within the flexure body first material web pockets (71) in an interference pattern.

20 Claims, 5 Drawing Sheets

(58) Field of Classification Search
CPC ...... A61M 2205/583; A61M 2205/588; A61M 2205/8212; A61M 2230/43; A62B 18/025; A62B 18/084; A62B 23/025; Y10T 24/4072
USPC ............ 128/201.11, 201.27, 202.27, 205.25, 128/205.27, 206.21, 206.24, 206.27, 128/207.11, 207.13, 845, 863, DIG. 23
See application file for complete search history.

(56) References Cited

U.S. PATENT DOCUMENTS

| | | |
|---|---|---|
| 2009/0250065 A1 | 10/2009 | Omura |
| 2010/0223706 A1 | 9/2010 | Becker |
| 2010/0224199 A1* | 9/2010 | Smith ................ A41D 13/1161 128/863 |
| 2011/0214674 A1 | 9/2011 | Ging |
| 2011/0220113 A1 | 9/2011 | Newman |
| 2016/0038708 A1 | 2/2016 | Amarasinghe |

FOREIGN PATENT DOCUMENTS

| | | | |
|---|---|---|---|
| JP | H0857055 A | 3/1996 | |
| JP | 2000325481 A | 11/2000 | |
| WO | WO2010066004 A1 | 6/2010 | |
| WO | WO 2011121466 A1 * | 10/2011 | ........ A61M 16/0683 |
| WO | WO2011121466 A1 | 10/2011 | |

* cited by examiner

UNIDIRECTIONAL FLEXION CLIP

CROSS-REFERENCE TO RELATED APPLICATIONS

This patent application claims the priority benefit under 35 U.S.C. §371 of international patent application no. PCT/IB2013/051554, filed Feb. 27, 2013, which claims the priority benefit under 35 U.S.C. §119(e) of U.S. Provisional Application No. 61/604,168 filed on Feb. 28, 2012, the contents of which are herein incorporated by reference.

BACKGROUND OF THE INVENTION

1. Field of the Invention

The present invention relates to a support member for a respiratory interface devices for communicating a flow of gas with an airway of a user such as, but not limited to, a mask, and, in particular, to a support for a respiratory interface device that is structured to flex substantially in one direction but not other directions.

2. Description of the Related Art

A variety of respiratory interface devices are known that cover the areas surrounding the nose and/or mouth of a human user and that are designed to create an effective fit against the user's face. Typically, gases can be provided at a positive pressure within the mask for consumption by the user. The uses for such masks include high altitude breathing (aviation applications), swimming, mining, fire fighting, and various medical diagnostic and therapeutic applications.

One requisite of many of these masks, particularly medical respiratory masks, is that they provide an effective fit against the user's face and that the mask contours with the user's face to limit or prevent leakage of the gas being supplied. The fit of a mask is partially controlled by the location of the couplings of the support assembly for the mask. That is, the support assembly for the mask is, typically, one or more straps, or other devices, that encircle the user's head. The support assembly couplings may attach at various locations about, or near, the perimeter of the mask. The location of the support assembly couplings on the mask effect the fit of the mask.

The location for the support assembly couplings to provide the best fit, however, may not always correspond to a convenient location for the support assembly couplings. For example, a flexible support assembly strap may be drawn inconveniently close to the user's eyes. This problem may be addressed by utilizing rigid support assembly couplings, e.g. rigid clips, that are disposed on the mask and may be used to reposition the location of the support assembly straps relative to the user's face. These rigid clips, typically, extend past the edge of the mask. In this configuration, however, the clips may engage the user's face and act as a lever to lift the mask off the user's face, thereby breaking the seal between the mask and the user's face.

SUMMARY OF THE INVENTION

One embodiment of the present invention provides a flexion coupling for a respiratory interface device, the respiratory interface device including a mask and a support assembly having at least one strap, the flexion coupling including an elongated flexure body with at least one mask coupling and at least one strap coupling, the at least one mask coupling structured to be coupled to the mask, and the at least one strap coupling structured to be coupled to the at least one strap.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 2A-2D are schematic isometric detail views of flexure bodies in which FIG. 2A shows a flexure body with square elements, FIG. 2B shows a flexure body with triangular elements, FIG. 2C shows a flexure body with nesting elements, and FIG. 2D shows a flexure body with alternate nesting elements;

FIG. 3A is a top view and FIG. 3B is a side view;

FIG. 5A is a side view, and FIG. 5B is a top view.

DETAILED DESCRIPTION OF EXEMPLARY EMBODIMENTS

Figure 1:
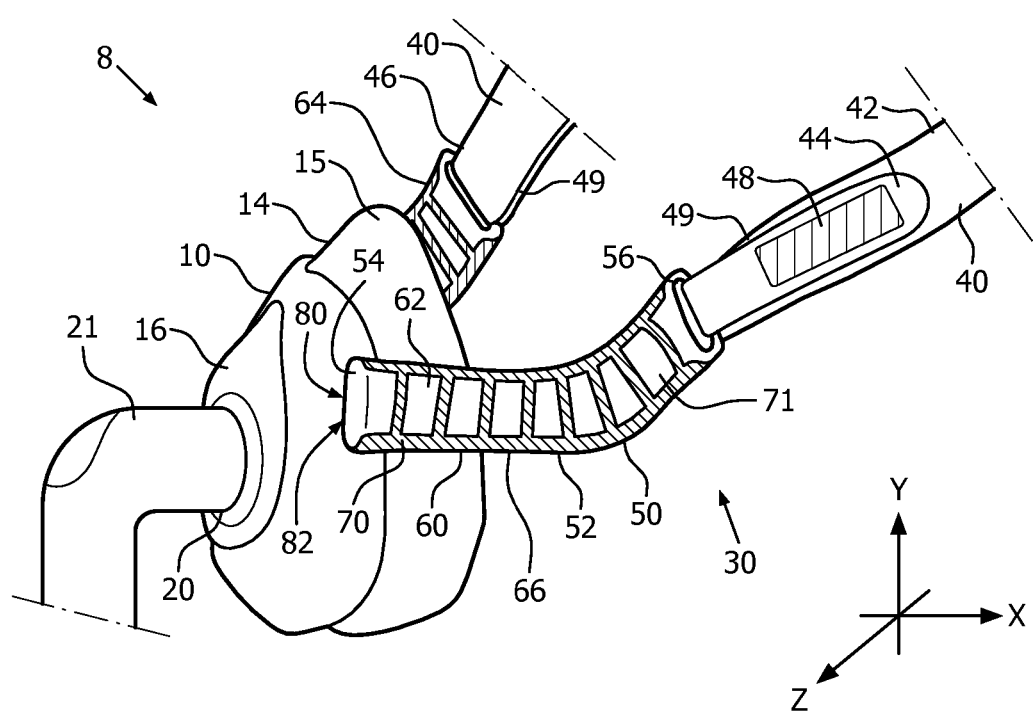
FIG. 1 is an isometric view of a respiratory interface device.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, a "coupling" is one element of a coupling assembly. That is, a coupling assembly includes at least two elements, or couplings, that are structured to be coupled together. It is understood that the elements of a coupling assembly correspond to each other. For example, in a coupling assembly, if one coupling element is a snap socket, the other coupling element is a snap plug, or, if one coupling element is a strap, the other coupling element may be a slot through which the strap extends.

As used herein, a "flexure body" is a body including flexible elements and rigid elements and which is structured to substantially flex in the direction of a primary axis in a three axis coordinate system. For example, a chain or an elastic member, e.g. a rubber band, may be flexed in virtually any direction as well as being stretched or compressed. An elongated, planar strip of tin, on the other hand, may be flexed when pressure is applied normal to the plane of the strip, but may not be substantially flexed in the plane of the strip or stretched/compressed. Thus, the strip of tin is structured to flex in the direction of one axis in a three axis coordinate system. Further, as used herein, a "flexure body" may be flexed minimally along the other, non-primary axes.

As used herein, an "interference pattern" means that separate rigid elements of a flexure body are disposed in a pattern such that, upon application of force in the direction of a primary axis, the rigid elements do not engage, or substantially engage, each other, but, upon application of force in the direction of a non-primary axis at least some of the rigid elements engage each other.

As used herein, a "web" is a thin, flexible, planar member that may, or may not, include filaments. That is, the "web" may be fabric but may also be a homogeneous material such as, but not limited to, a semi-rigid gel. Further, the "web" may include more than one layer, such as, but not limited to, a semi-rigid gel disposed within a membrane.

As used herein, "engage" means that two elements contact each other, or, two elements compress a non-fluid third element therebetween such that the two elements may not be moved closer together. That is, the third element effectively creates the contact between the two elements. As used herein, a "pocket" is a plenum that may have an opening or may be sealed.

As shown in FIG. 1, a respiratory interface device 8 includes a respiratory mask 10 and a support assembly 30, which is also typically referred to as a headgear, for holding the mask on the head of the user. Mask 10 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV™) device, proportional positive airway pressure (PPAP) device, C-Flex™ device, Bi-Flex™ device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

In an exemplary embodiment of the present invention, mask 10 is an oral/nasal mask structured to accommodate both the oral and nasal regions of the user's face. An upper portion 14 can accommodate the nasal region, and a lower portion 16 can accommodate the oral region. Mask 10 also includes a patient contacting cushion 15. In an exemplary embodiment, cushion 15 is integrally connected to upper portion 14 and lower portion 16. Cushion 15 is structured to extend toward the user's face and generally defines the depth of mask 10. The present invention contemplates, however, that mask 10 can be any patient interface or other device that contacts the user. For example, the present invention contemplates that mask 10 can be a nasal mask, a cannula, nasal pillows, a total face mask—that is provided around the entire perimeter of the face, or any other device that is to be held on the head of the user.

Mask lower portion 16 also defines a lower opening 20. Lower opening 20 can function as a gas inlet. In the embodiment shown in FIG. 1, gas inlet (lower opening 20) can be coupled to a coupling device 21, such as a swivel conduit, for carrying gas such as air between mask 10 and an external gas source (not shown), such as a blower, or any other suitable device. It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure therapy, as noted above.

The particular coupling device 21 shown in FIG. 1 is not meant to be limiting and it should be understood that the present invention contemplates a variety of different coupling devices that could be attached, either permanently or selectively, to lower opening 20 to carry gas to or from mask 10. Thus, a variety of coupling devices (e.g., with or without swivels on one or both ends, and with or without an exhalation system formed integral to the device) may be substituted for coupling device 21.

Support assembly 30 includes at least one strap 40 and at least one flexion coupling 50. At least one strap 40 has an elongated body 42 (shown in part) structured to encircle the user's head. Strap body 42 may be a tension member, elastic, or a combination thereof. Strap body 42 has a first end 44 and a second end 46. Strap ends 44, 46 may each include hook-and-loop couplings 48 structured to allow strap ends 44, 46 to be folded back upon themselves and attached, thereby forming loops 49. As shown, there is a single strap body 42, but it is understood that support assembly 30 may include a plurality of strap bodies 42.

Flexion coupling 50 includes an elongated flexure body 52 with at least one mask coupling 54 and at least one strap coupling 56. Flexure body 52 is elongated and generally planar in an initial configuration. As described below, flexure body 52 may be deformed, i.e. placed into a curved configuration, during use. Mask coupling 54 is structured to be coupled to mask 10, and strap coupling 56 is structured to be coupled to strap 40. For example, strap coupling 56 may be a slot in flexure body 52 through which strap loop 49 may extend. Mask coupling 54 may be a temporary coupling, such as, but not limited to, a snap.

Alternatively, mask coupling 54 may be a fixed coupling. Flexure body 52 includes a first material 60 and a second material 62. Flexure body first material 60 has a first hardness and flexure body second material 62 has a second hardness. Flexure body second material 62 second hardness being greater than flexure body first material 60 first hardness. In an exemplary embodiment, flexure body first material 60 is silicone and flexure body second material 62 is a rigid polymer. It is understood, however, that flexure body first material 60 may be other flexible materials, such as, but not limited to, rubber, elastic polymers, semi-rigid gels, and fabric or other flexible sheet-like materials. Further, flexure body second material 62 may be other rigid materials, such as, but not limited to, metal, wood, semi-rigid gel (which is harder than a semi-rigid gel being used as a first material), or a non-elastic polymer.

Flexure body first material 60 is substantially flexible and forms an elongated web 70. Web 70 may be a unitary body. Web 70 may be elongated, generally planar, and straight but, in an exemplary embodiment, web 70 is elongated, generally planar, and may include at least one curve within the plane of flexure body 52. In this configuration, flexion coupling 50 may be positioned so as to not interfere with the user's vision or otherwise be uncomfortable. Flexure body 52 has an inner side 64 and an outer side 66. Flexure body inner side 64 is disposed adjacent to the user's face and flexure body outer side 66 is disposed opposite flexure body inner side 64. Web 70 defines two or more, and typically many more, pockets 71. Typically, there is one pocket 71 for each second material body 82, discussed below. In an exemplary embodiment, pockets 71 have generally the same shape as second material bodies 82 disposed therein.

Flexure body second material 62, as noted above, is substantially inflexible and includes a plurality of elements 80. Flexure body second material elements 80 are coupled to web 70 and, in an exemplary embodiment, are disposed therein. Each flexure body second material element 80 has a body 82 which, in an exemplary embodiment, is generally planar. Flexure body second material element body 82 are, in an exemplary embodiment, between about 0.5 mm and about 5.0 mm thick and may be about 1.0 mm thick. While flexure body second material elements 80 having different shapes may be used on one flexure body 52, in an exemplary embodiment, flexure body second material elements 80 have a substantially similar size and shape. That is, as shown in FIGS. 2A-2D, exemplary shapes include square planar bodies 82A (FIG. 2A), triangular planar bodies 82B (FIG. 2A), and nesting bodies 82C (FIG. 2C), having at least one socket 84 and at least one corresponding plug 86. In nesting bodies 82C, a plug 86 disposed on one nesting body 82C is structured to fit within a socket 84 on an adjacent nesting body 82C.

Figure 2A:
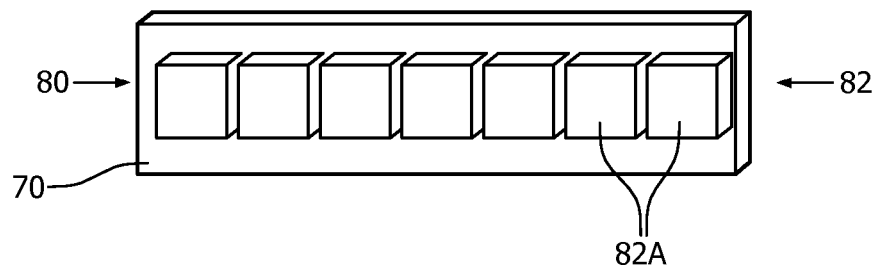
Figure 2B:
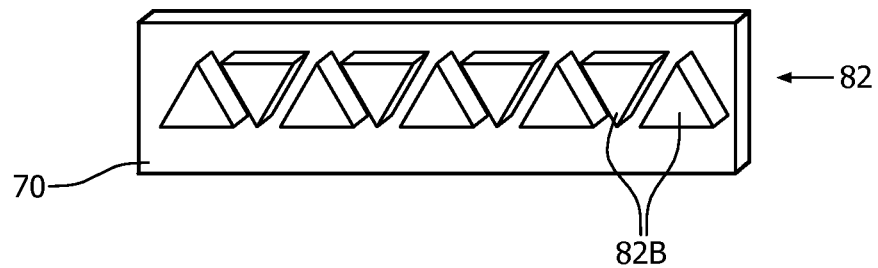
Figure 2C:
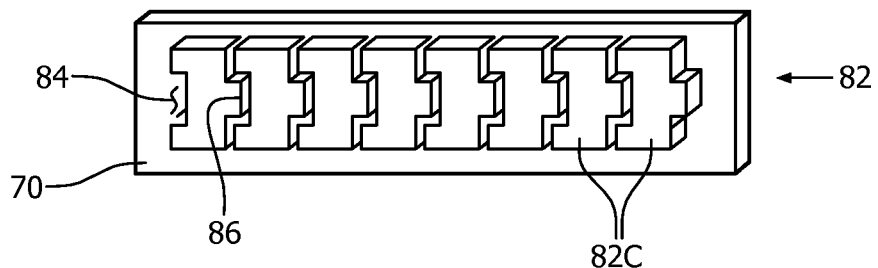
Figure 2D:
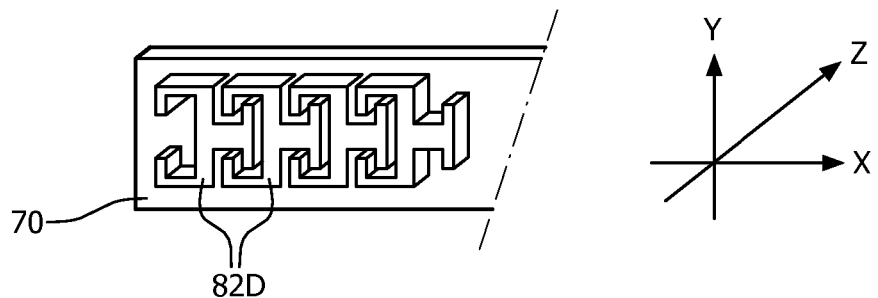

An alternative nesting body 82D, discussed below, is shown in FIG. 2D. It is noted that the shape, including the thickness, of second material bodies 82 effect the amount of flexure within flexure body 52. For example, square planar bodies 82A define a hinge extending over the adjacent sides of, and beyond, square planar bodies 82A. Conversely, the hinges defined by triangular planar bodies 82B extend into each other at the corners of triangular planar bodies 82B; thus, with triangular planar bodies 82B, the flexure body 52 is stiffer than with square planar bodies 82A.

As noted above, and in an exemplary embodiment, second material bodies 82 are each disposed in pocket 71 in web 70. Pockets 71, like second material bodies 82 are generally planar. The plane of pockets 71 are generally parallel with the plane of web 70. Web 70 may be formed about second material bodies 82 thereby forming pockets 71 and disposing second material bodies 82 therein simultaneously. Alternatively, pockets 71 may be formed into web 70 prior to placing second material bodies 82 into pockets 71. For example, a fabric web may have a second layer of fabric coupled thereto and divided into pockets 71, or, a gel web may have pockets 71 cut therein. Second material bodies 82 may then be placed in pockets 71 and pockets 71 may be sealed or otherwise closed. In an alternative embodiment, not shown, second material bodies 82 are coupled to one surface of web 70. That is, material bodies 82 are disposed on the surface of web 70.

Flexure body second material elements 80 are, in an exemplary embodiment, disposed in an interference pattern. That is, in an exemplary embodiment, flexure body second material elements 80 are disposed immediately adjacent each other and are generally in the same plane as adjacent flexure body second material elements 80. In an exemplary embodiment, flexure body second material elements 80 are spaced between about 0.5 mm and 5.0 mm from each other and, in an exemplary embodiment are spaced about 1.0 mm from each other. If web 70 defines a curve, the shape of second material bodies 82 may be adapted to maintain the interference pattern over the curved portion of web 70. For example, if second material bodies 82 are generally rectangular, at the location of the curve in web 70 an arcuate second body (not shown) may be provided. Alternatively, as shown in FIG. 1, second material bodies 82 adjacent the curved portion of web 70 may have the lateral sides angled relative to each other, i.e. second material bodies 82 may have a slightly trapezoidal shape.

In this configuration, flexure body second material elements 80 engage each other when a force is applied along a non-primary axis. That is, as used herein, and as shown best in FIGS. 3A and 3B, a three axis coordinate system shall be used with the x-axis extending generally along the longitudinal direction of flexure body 52, the y-axis extends perpendicular to the x-axis in the plane of flexure body 52, and the z-axis extends normal to the plane of flexure body 52. In this configuration, and as used herein, the z-axis shown in the FIGS. is the primary axis and the x-axis and y-axis are the non-primary axes. Further, it is understood that any force applied to flexure body 52 at an angle relative to any axis may be decomposed into portions aligned with the coordinate axes. Thus, if a force is applied to flexure body 52 at an angle relative to any axis, flexure body 52 may move in the direction of the primary axis in response to the decomposed force aligned with the primary axis, while movement in response to the decomposed forces aligned with the non-primary is resisted.

Figure 3A:
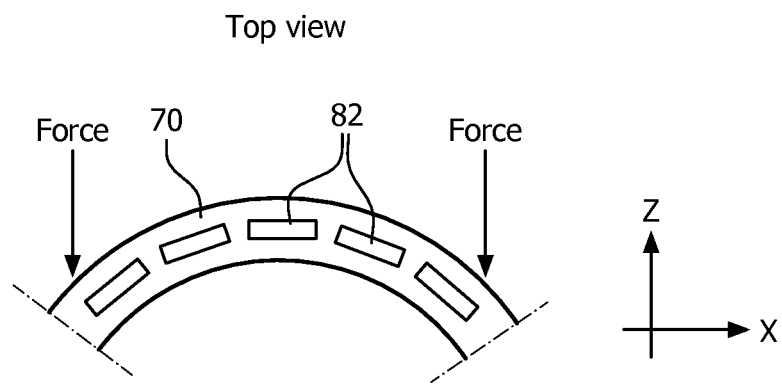
FIGS. 3A-3B are schematic views of flexure bodies having a force applied thereto.
Figure 3B:
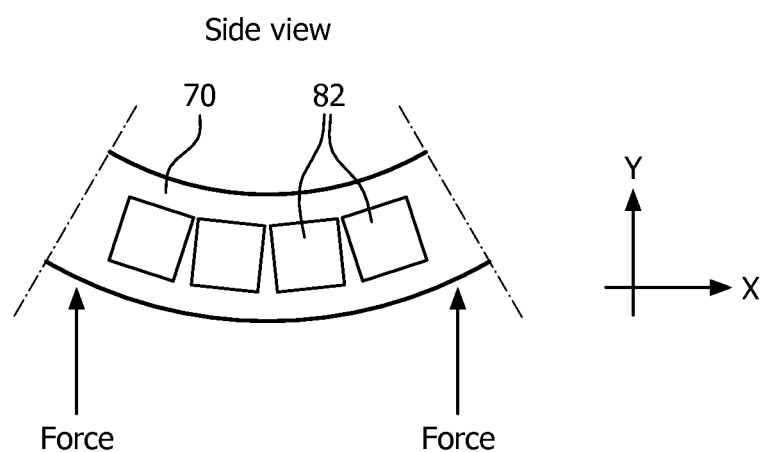

Thus, as shown in FIG. 3A, when a force is applied to flexure body 52 along the primary axis, flexure body 52 may bend without flexure body second material elements 80 substantially engaging each other. Conversely, as shown in FIG. 3B, when a force is applied to flexure body 52 along a non-primary axis, flexure body second material elements 80 engage each other and resist bending. Thus, the engagement of flexure body second material elements 80 substantially prevents flexure body 52 from bending within the plane of flexure body 52. Further, engagement of flexure body second material elements 80 further prevents the compression of flexure body 52 in a direction corresponding to the longitudinal axis of flexure body 52. Further, if flexure body second material elements 80 are nesting bodies 82D, nesting bodies 82D may be shaped, as shown in FIG. 2D, to resist the stretching of flexure body 52.

In another exemplary embodiment, flexure body second material elements 80 are not disposed in an interference pattern. That is, alternate flexure body second material elements 80 may be disposed, generally, on opposite sides of web 70 such that adjacent flexure body second material elements 80 are not in the same general plane. For example, alternate flexure body second material elements 80 may be disposed alternately on web inner and outer sides 64, 66, or, web 70 may be made sufficiently thick so as to enclose flexure body second material elements 80 in two different planes. In this configuration, and when a force is applied in a non-primary direction, stress concentration at the edges of pockets 71 resist bending in the non-primary directions. Flexure body 52 may, however, still flex in the direction of the primary axis.

Figure 4:
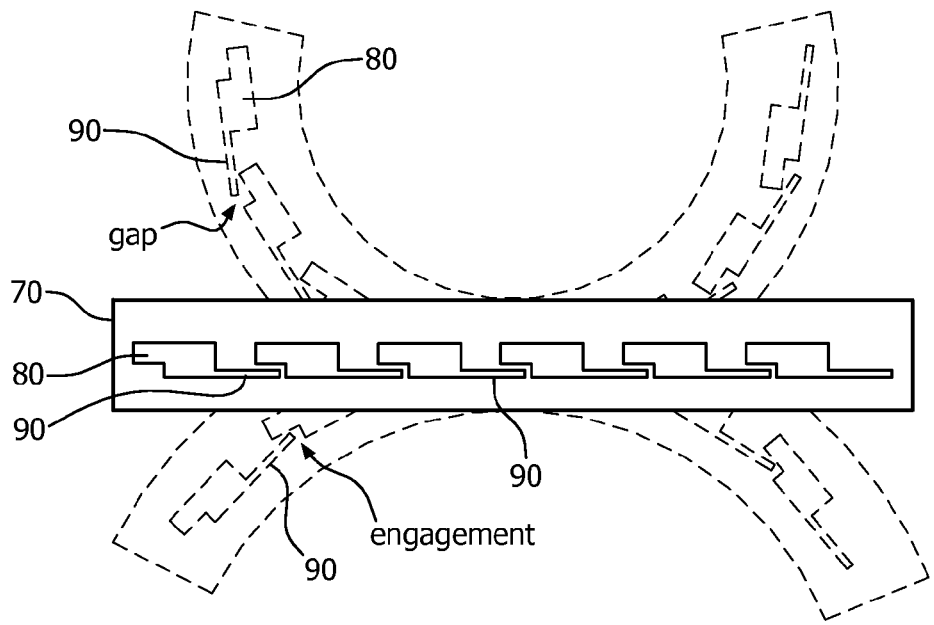
FIG. 4 is a schematic top view of an alternate flexure body.

As shown in FIG. 4, flexure body second material elements 80 may also be shaped to limit the bending of flexure body 52. That is, at least one element of flexure body second material plurality of elements 80 includes a stop member 90. Each stop member 90 is disposed on one of the inner side or outer side of the associated second material element 80. In an exemplary embodiment, each stop member 90 is thinner than second material bodies 82 from which it extends. In an exemplary embodiment, each stop member 90 is disposed adjacent to one of the inner or outer sides of second material bodies 82 from which it extends. That is, in an exemplary embodiment, each stop member 90 is not disposed at the middle of the plane defined by second material bodies 82 from which it extends. Each stop member 90 extends toward an adjacent second material element 80 and is structured to engage an adjacent second material element 80 at one of the inner or outer sides of the adjacent second material element 80 upon a selected amount of flexure of the flexure body. The engagement of stop member 90 with an adjacent second material element 80 limits the degree of bending of flexure body 52 in one direction along the primary axis.

Figure 5A:
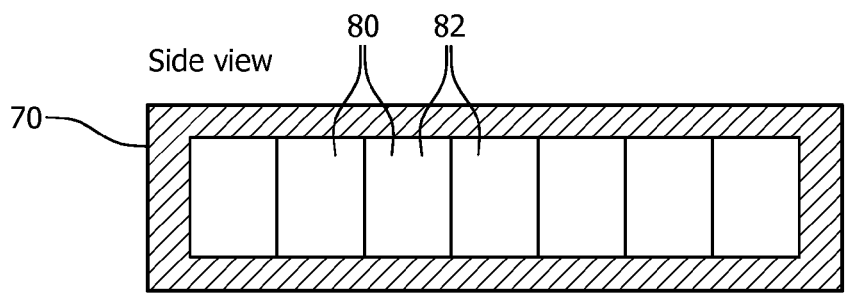
FIGS. 5A and 5B show an alternate flexure body.
Figure 5B:
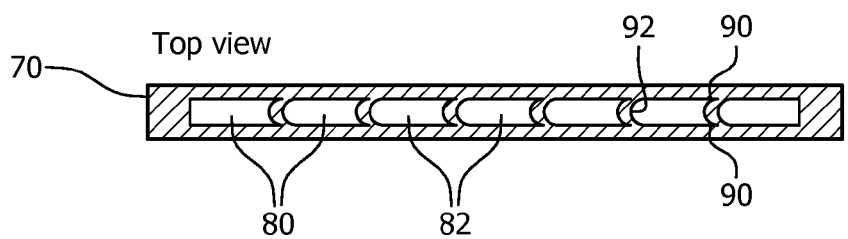

In another embodiment, shown in FIGS. 5A and 5B, at least one element of flexure body second material plurality of elements 80 includes two stop members 90. Stop members 90 are disposed, one each, on the inner side and the outer side of the associated second material element 80. In this configuration, stop members 90 form a groove 92 into which an adjacent second material element body 82 extends. It is noted that in this configuration, plurality of second material elements 80 do not have visible gaps therebetween.

When assembled, at least one mask coupling 54 is coupled to mask 10 and at least one strap coupling 56 is coupled to at least one strap 40. In an exemplary embodiment, there are at least two flexion couplings 50 with one flexion coupling 50 coupled to each of strap first end 44 and strap second end 46. In use, the primary axis for flexion couplings 50 extends generally normal to that portion of the user's face disposed under flexion coupling 50. Thus, flexion couplings 50 may flex in a direction generally normal to the user's face while otherwise maintaining their shape.

Figure 6:
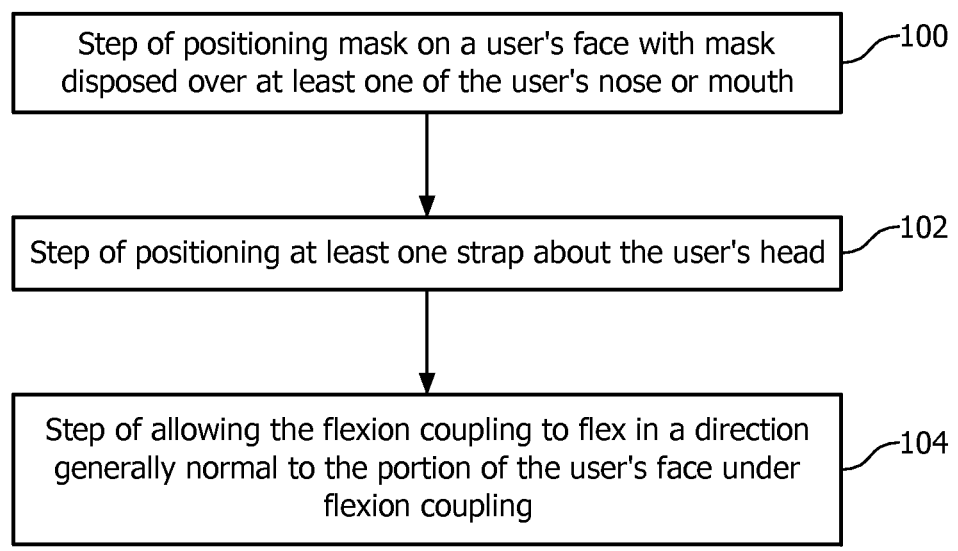
FIG. 6 is a flow chart of the steps of the associated method.

As shown in FIG. 6, the method of using respiratory interface device 8 described above includes the steps of positioning 100 mask 10 on a user's face with mask 10 disposed over at least one of the user's nose or mouth, positioning 102 at least one strap 42 about the user's head, and allowing the flexion coupling 50 to flex 104 in a direction generally normal to the portion of the user's face under flexion coupling 50. In another embodiment, not shown, flexure body 52 extends over mask 10 and is coupled thereto at a single mask coupling 54.

In the exemplary embodiment detailed above, web 70 is described as being planar. It is noted that web 70 may be shaped so as to not be planar and generally follow the contour of a user's face. In this embodiment, not shown, flexure body second material elements 80 are still disposed immediately adjacent each other and are generally in the same plane as adjacent flexure body second material elements 80. Spaced flexure body second material elements 80, however, may be in different planes. That is, assuming there are ten locations for flexure body second material elements 80, flexure body second material element 80 in the second location is generally in the same plane as adjacent flexure body second material elements 80 located in the first and third locations. But, flexure body second material element 80 in the second location may not be in generally the same plane as flexure body second material element 80 in the tenth location.

This offsetting is accomplished by having one or more consecutive flexure body second material elements 80, as well as pockets 71, offset in the same direction while still being in the same general plane. That is, flexure body second material elements 80, as well as their associated pockets 71, are positioned such that adjacent flexure body second material elements 80 will engage each other when a force is applied in a non-primary direction. For example, if flexure body second material elements 80 are 1.0 mm thick, a flexure body second material element 80 at the first location may be 4.0 mm from flexure body outer side 66; a flexure body second material element 80 at the second location may be 3.8 mm from flexure body outer side 66; a flexure body second material element 80 at the third location may be 3.6 mm from flexure body outer side 66; and so on. In this configuration, adjacent flexure body second material elements 80 are still disposed generally in the same plane but spaced flexure body second material elements 80 may be in different planes.

It can be appreciated from the foregoing that the present invention provides a respiratory interface device support coupling capable of flexing around the user's face while maintaining the rigidity of the coupling in the direction needed to maintain the flexible support assembly strap in a configuration that is comfortable for the user.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A flexion coupling for a respiratory interface device, the respiratory interface device including a mask and a support assembly having at least one strap, the flexion coupling comprising:
    an elongated flexure body with at least one mask coupling and at least one strap coupling;
    the at least one mask coupling structured to be coupled to the mask; and
    the at least one strap coupling structured to be coupled to the at least one strap.

2. The flexion coupling of claim 1, wherein:
    the flexure body includes a first material and a second material;
    the flexure body first material having a first hardness;
    the flexure body second material having a second hardness; and the flexure body second material second hardness being greater than the flexure body first material first hardness.

3. The flexion coupling of claim 2, wherein:
the flexure body first material is substantially flexible and forms an elongated web;
the flexure body second material is substantially inflexible and includes a plurality of elements; and
the flexure body second material plurality of elements being coupled to the flexure body first material web.

4. The flexion coupling of claim 3, wherein:
the web includes at least two pockets; and
the flexure body second material plurality of elements are disposed within the flexure body first material web pockets.

5. The flexion coupling of claim 3, wherein the flexure body second material plurality of elements are disposed in an interference pattern.

6. The flexion coupling of claim 3, wherein:
the flexure body second material plurality of elements each have a substantially similar size and shape; and
the flexure body second material plurality of elements are spaced between about 0.5 mm and about 5.0 mm from each other.

7. The flexion coupling of claim 6, wherein the flexure body second material plurality of elements are spaced about 1.0 mm from each other.

8. The flexion coupling of claim 6, wherein:
the flexure body is generally planar and has an inner side and an outer side;
at least one element of the flexure body second material plurality of elements includes a stop member;
each stop member disposed on one of the inner side or outer side of the associated second material element; and
each stop member extending toward an adjacent second material element and structured to engage the adjacent second material element upon a selected amount of flexure of the flexure body.

9. The flexion coupling of claim 2, wherein:
the flexure body is generally planar and has an inner side and an outer side; and
the flexure body including at least one curve within the plane of the flexure body.

10. The flexion coupling of claim, 2 wherein:
the first material is silicone; and
the second material is a rigid polymer.

11. A respiratory interface device comprising:
a mask and a support assembly;
the support assembly having at least one strap and at least one flexion coupling;
the flexion coupling having an elongated flexure body with at least one mask coupling and at least one strap coupling;
the at least one mask coupling structured to be coupled to the mask;
the at least one strap coupling structured to be coupled to the at least one strap;
the flexion coupling at least one mask coupling coupled to the mask; and
the flexion coupling at least one strap coupling coupled to the at least one strap.

12. The respiratory interface device of claim 11, wherein:
the flexure body includes a first material and a second material;
the flexure body first material having a first hardness;
the flexure body second material having a second hardness; and
the flexure body second material second hardness being greater than the flexure body first material first hardness.

13. The respiratory interface device of claim 12, wherein:
the flexure body first material is substantially flexible and forms an elongated web;
the flexure body second material is substantially inflexible and includes a plurality of elements; and
the flexure body second material plurality of elements being coupled to the flexure body first material web.

14. The respiratory interface device of claim 13, wherein:
the web includes at least two pockets; and
the flexure body second material plurality of elements are disposed within the flexure body first material web pockets.

15. The respiratory interface device of claim 13, wherein the flexure body second material plurality of elements are disposed in an interference pattern.

16. The respiratory interface device of claim, 13 wherein:
the flexure body second material plurality of elements each have a substantially similar size and shape; and
the flexure body second material plurality of elements are spaced between about 0.5 mm and about 5.0 mm from each other.

17. The respiratory interface device of claim 16, wherein the flexure body second material plurality of elements are spaced about 1.0 mm from each other.

18. The respiratory interface device of claim 16, wherein:
the flexure body is generally planar and has an inner side and an outer side;
at least one element of the flexure body second material plurality of elements includes a stop member;
each stop member disposed on one of the inner side or outer side of the associated second material element; and
each stop member extending toward an adjacent second material element and structured to engage the adjacent second material element upon a selected amount of flexure of the flexure body.

19. The respiratory interface device of claim 12, wherein the first material is silicone; and the second material is a rigid polymer.

20. A method of using a respiratory interface device, the respiratory interface device having a mask and a support assembly, the support assembly having at least one strap and at least one flexion coupling, the flexion coupling having an elongated flexure body with at least one mask coupling and at least one strap coupling, the at least one mask coupling structured to be coupled to the mask, the at least one strap coupling structured to be coupled to the at least one strap, the flexion coupling at least one mask coupling coupled to the mask, and the flexion coupling at least one strap coupling coupled to the at least one strap, the method comprising:
positioning the mask on a user's face with the mask disposed over at least one of the user's nose or mouth;
positioning the at least one strap about the user's head; and
allowing the flexion coupling to flex in a direction generally normal to the portion of the user's face under the flexion coupling.

* * * * *